etc.

United States Patent [19]

Shen et al.

[11] Patent Number: 5,093,256

[45] Date of Patent: Mar. 3, 1992

[54] ESSENTIALLY PURIFIED, THERMOSTABLE AND ALKALOPHILIC LIPASE FROM BACILLUS SP. A30-1 ATCC 53841

[76] Inventors: Gwo-Jenn Shen, 4317 Tacoma Blvd., Okemos, Mich. 48864; Kailash C. Srivastava, 3940 Trailwood Dr., Okemos, Mich. 48864; Yongxiang Wang, 705-204 Cherry La., East Lansing, Mich. 48823; Henry Y. Wang, 2488 Bunker Hill Rd., Ann Arbor, Mich. 48105

[21] Appl. No.: 314,677

[22] Filed: Feb. 22, 1989

[51] Int. Cl.⁵ .................. C12N 9/20; C12N 15/75
[52] U.S. Cl. ..................... 435/198; 435/832
[58] Field of Search .................. 435/198, 134, 832

[56] References Cited

U.S. PATENT DOCUMENTS

| | | | |
|---|---|---|---|
| 4,444,886 | 4/1984 | Esders et al. | 435/198 |
| 4,732,853 | 3/1988 | Whitesides et al. | 435/198 |
| 4,798,793 | 1/1989 | Eigtved | 435/198 |

FOREIGN PATENT DOCUMENTS

| | | | |
|---|---|---|---|
| 117553 | 9/1984 | European Pat. Off. | |
| 0257388 | 3/1988 | European Pat. Off. | 435/134 |
| 57-63087 | 4/1982 | Japan . | |
| 62-79782 | 4/1987 | Japan . | |
| 62-210986 | 9/1987 | Japan . | |
| 63-39579 | 2/1988 | Japan . | |

OTHER PUBLICATIONS

Bozoglu et al, *Isolation and Characterization* . . . , J. Agric. Food Chem., 32, pp. 2–6, 1984.
*Thermophilic Bacterial Isolates Producing Lipase,* FEMS Microbiol. Lett., 48:339–343, 1987, Pauline Gowland, Martin Kernick and Trichur K. Sundaram.
*A Thermostable Bacillus Lipase Res. Disclosure,* 1987, 275:121.
*Lipase Production by Bacillus Stearothermophilus S.203 in Shake Flasks,* Zbl. Mikrobiol. 139, 61–68, 1984, M. S. Ammar and L. E. McDaniel.

*Primary Examiner*—Douglas W. Robinson
*Assistant Examiner*—Michael Meller
*Attorney, Agent, or Firm*—Quarles & Brady

[57] ABSTRACT

A thermostable lipase is produced by aerobically culturing a microorganism having the identifying characteristics of Bacillus sp. A30-1 ATCC No. 53841 on a nutrient medium under growth conditions until a recoverable lipolytic activity is detectable and thereafter isolating the thermostable lipase. The thermostable lipase has an optimum pH of 9.5, an isoelectric point of 5.15, a molecular weight of about 65,000 and retaining approximately 100% of its original activity upon being heated at 75° C. for 30 minutes.

1 Claim, No Drawings

ESSENTIALLY PURIFIED, THERMOSTABLE AND ALKALOPHILIC LIPASE FROM BACILLUS SP. A30-1 ATCC 53841

FIELD OF THE INVENTION

The present invention relates to enzymes. More particularly it relates to lipases or lipolytic enzymes.

BACKGROUND OF THE INVENTION

Lipases are enzymes that hydrolyze tri-, di-, and mono-glycerides. Triglycerides of long-chain fatty acids are the natural substrates of lipases and are insoluble in water. Lipases are characterized by their ability to rapidly catalyze the hydrolysis of ester bonds at the interface between the insoluble substrate phase and the aqueous phase in which the enzyme is soluble. The ability to catalyze hydrolysis of insoluble long-chain fatty acid esters distinguishes lipases from other esterases which catalyze hydrolysis of soluble esters in preference to insoluble esters.

Lipases are produced by plants, animals, and microbial species. A wide variety of microorganisms (including yeasts, molds and bacteria) are sources of lipases. Microbial lipases from the yeasts, Candida and Torulopsis, molds such as Rhizopus, Penicillium, Aspergillus, Geotrichum and Mucor and bacteria of the genera Pseudomonas, Achromobacter, and Staphylococcus have been found.

Most of these microbial enzymes are extracellular and in some instances inducible with various substrates. The formation of the enzyme is feedback regulated by mono- and di-saccharide and glycerol in the growth medium. Some microbial lipases are glycosylated and the sugar moiety is thought to facilitate the passage of the enzyme through the cell wall into the growth medium.

There are a number of industrial applications for microbial lipases. They are the following:

A. Hydrolysis of Oils and Fats

A number of patents have been issued relating to the use of lipases as catalysts for the hydrolysis of oils and fats to produce fatty acids and glycerol, e.g. U.S. Pat. Nos. 4,629,742 and 4,678,580. Enzymatic hydrolysis of triglycerides can be used as a low energy consuming alternative to the present steam (Colgate-Emery) process. The use of enzymatic catalysis may also yield products of better odor and color. It gives a cheaper overall process if immobilized lipase can be used. Unfortunately, the non-specific lipase from Candida spp. used in the aforementioned patents has an optimal temperature of less than 42° C. Ideally, the enzyme should have an operating temperature range which is above the melting point of the feedstock, such as BFT, Bleachable Fancy Tallow. It also has been suggested that enzymatic hydrolysis could provide a useful method of generating fatty acids from unstable oils such as those containing highly unsaturated fatty acid residues, e.g. fish oils.

B. Interesterification of Oils and Fats

Interesterification is a process which is used in the oils and fats industry to modify the composition and hence the physical properties of triglyceride mixtures. The ability to produce novel triglycerides mixtures is of industrial interest because some of the mixtures have valuable properties. For example, 1,3-specific lipase-catalyzed interesterification of 1,3-dipalmitoyl-2-oleoyl glycerol (POP), which is a major triglyceride of palm oil, with either stearic acid or tristearin gives products similar to cocoa butter, a more expensive product. Similarly, it is feasible to enrich an oil with the polyunsaturated fatty acid, such as linoleic acid by using a free fatty acid-containing mixture of saturated and unsaturated fatty acids.

C. Esterification of Fatty Acids

The lipase reaction is reversible and thus enables the enzymes to be used to catalyze the formation of esters from alcohol and fatty acids. It has been demonstrated that glycerides are produced by incubation of microbial lipases with a mixture of fatty acids and glycerol-water. Esters have been formed by the reaction of fatty acids with primary and secondary alcohols and diols in the presence of lipase.

D. Flavor Development in Dairy Products

The development of flavor in many dairy products is primarily due to the action of lipolytic enzymes on milk fat. Therefore, these enzymes can be used to enhance flavor formation in cheeses and to produce butter and cheese flavor preparations from butter oil and whole milk powder. Recently, it has been shown that some fungal lipases can be substituted for animal pregastric esterases as a flavor agent to enhance the flavor in cheese manufacturing (see U.S. Pat. No. 4,726,954).

E. Applications in Detergent Industry

Several patents have been issued relating to the use of microbial lipases in the formulation of laundry detergents. The addition of lipases to both pre-wash soaking agents and detergent powders has been advocated.

Recently, the fungal lipase gene from mesophilic Humicola lanuginosa has been introduced into an industrial production host of Aspergillus spp. The enzyme thus produced removes fatty stains at temperatures from 15° C. to 60° C. and has a pH optimum of 9 or higher. It is primarily used in detergent formulations and is commercially available in Japan. Microbial lipases have also been recommended for application in the removal of fatty deposits in dishwashing products, leather manufacture and sewage treatment.

There is still a need for a superior thermostable lipase, especially one of food grade.

SUMMARY OF THE INVENTION

The present invention relates to a thermostable lipase, which is obtained from the microorganism Bacillus sp. A30-1 ATCC No. 53841.

The microorganism which produces the lipase of the present invention has an optimum temperature for growth of about 60° C. to about 65° C. and it has an optimum growth pH of about 7.0 to about 9.0. The lipase that is produced is stable and retains 100% of enzyme activity at 60° C. for 2 hours. It retains 90-95% activity at pHs of from 5 to 11 for 15 hours. It also is functional over a wide range of pH's from about 4.5 to about 10. It has an optimum pH for activity of 9.5, but shows 90% activity between 4.5 and 10.

The lipase of the present invention has the following additional physiochemical properties:

(1) Reactivity: It hydrolyzes fats and oils to produce fatty acids and glycerol.

(2) Influence of inhibitors: Its activity is not destroyed by hydrogen peroxide or alkaline proteases.

The lipase of the present invention is produced by aerobically culturing a substantially pure culture of lipase producing microorganism having the identifying physical characteristics of Bacillus sp. A30-1 ATCC No. 53841 in a nutrient medium under growth conditions until substantial lipolytic activity is detectible and thereafter isolating the thermostable lipase.

DESCRIPTION OF PREFERRED EMBODIMENT

In the preferred embodiment of the grant invention, the lipase is produced by aerobically culturing a biologically pure culture of Bacillus sp. A30-1 ATCC No. 53841 on a substrate of corn oil. The microorganism is able to grow at 60° to 65° C. in the pH range of 6-9 and it produces the lipase extracellularly when grown on corn oil as a substrate. Since the enzyme is produced extracellularly, it is easy to recover. Bacillus spp. are the organisms of choice for the production of food grade industrial enzymes as they are considered to be food safe (GRAS).

The practice of the invention is further illustrated by the experimental work which is described hereinafter.

EXPERIMENTAL

Materials and Methods

Source of Thermophilic Isolates

The sediment samples for screening for thermophilic microorganisms were obtained from the hot springs of Yellowstone National Park.

Screening for Lipolytic Microorganisms

Samples were incubated on plates of (basic) screening medium (Table 1) containing 2% agar. After autoclaving, the pH of the medium was adjusted to 9.0 with 1M glycine - NaOH buffer. Prior to pouring the plates, the substrate mixture consisting of 50% corn oil and 50% Tween 80 was added asseptically to a final concentration of 0.5%. Rhodamine B (1 mG/mL stock solution) was added at the rate of 1 mL/100 mL of the final medium. All the components of the medium were thoroughly mixed and plates were poured. One gram of each of the sediment samples was suspended in 10 mL of screening medium without agar at pH 9.0 and inoculated at 10> dilution on the plates of Rhodamine B prepared previously. The plates were incubated for up to a week in humid chambers at 60° C. Colonies exhibiting orange fluorescent halo with UV irradiation were regarded positive lipase producers.

Isolation of Microorganism

The lipase producing colonies were inoculated into the above described basic screening broth medium for 4 passages. Subsequently, the culture was diluted and replated on agar plates containing Rhodamine B. Single colonies were grown for several passages to ascertain the purity of culture. Out of the many lipolytic organisms, pure cultures of Bacillus sp. A30-1 ATCC No. 53841 were selected for further studies. The organism was cultivated in 200 mL of the screening medium without agar contained in an erlenmeyer flask of 1 liter capacity. Corn oil (final concentration 0.1%) was the carbon source.

Lipase Assays

Lipase production was routinely assayed by monitoring the fatty acid released from corn oil. The assay is based on the fact that the dye Rhodamine 6G in benzene solution reacts with an acid to form a chromophore which can be spectrophotometrically quantified. One tenth mL of cell free culture broth (obtained by removing cells by centrifugation) was mixed with 0.02 mL of a 25% corn oil solution in 100 mM Tris-Hcl buffer (pH 9.5) and then incubated at 60° C. for 1 hr. After appropriate time the reaction was stopped with the addition of 0.1N HCl in 95% ethanol. The resulting fatty acids were extracted with petroleum ether, and evaporated to dryness under vacuum. Subsequently, diluted Rhodamine 6G stock solution was added. After fifteen minutes at room temperature the absorbance of the resulting reaction mixture was read at 515 nm. One unit of lipase is defined as the amount that will liberate 1 $\mu$mole of fatty acid per hour under the assay condition.

Alternatively, using the modified method of Tserng et al.[1], the lipase was assayed by gas chromatography. The dried extract obtained in the manner described above was dissolved in 50 $\mu$L of hexane containing 20 $\mu$g of heptade-canoic acid (C17:0, which is not present in the corn oil substrate and was used as an internal standard). The addition of heptadecanoic acid facilitated the identification and quantification of free fatty acids. This preparation was injected into a Hewlett Packard GC.

The conditions for gas chromatography were as follows:

Column glass, 0.25 inch O.D., 2 mm I.D., length 6 ft. packed with 5% DEGS-ps on 100/120 Supelcoport. Injector temperature 220° C., oven temperature 220° C., detector temperature 250° C., carrier gas: nitrogen at 25 mL/min. Detector: flame ionization.

One unit of lipase is defined as the amount that will liberate 1 $\mu$mole of fatty acid per hour under the assay condition.

Production of Thermostable Lipolytic Enzyme

The following example illustrates the production of the lipolytic enzyme from thermophilic Bacillus sp. A30-1 (ATCC No. 53841).

EXAMPLE 1

Inoculum Preparation

Colonies of Bacillus sp. A30-1 (ATCC No. 53841) were preserved in 10% glycerol vials (at −80° C.) or agar slants (basic medium contained 1% corn oil). The stock cultures were transferred to flasks (250 ml volume) which contain 25 mL liquid medium (basic medium with 0.5% corn oil w/o Tween 80). The flasks were then incubated at 60° C. with shaking (200 rpm) for 15-24 hrs.

Fermentation with 1 L Jar Fermentors

The fermentations were carried out in a 1 L fermentor (Multigen, New Brunswick, Co.) with working volume of 500 mL. The inoculum (1%) was aseptically transferred to the fermentor containing the medium (Basic medium with 1% corn oil, 1% Tween 80, 0.1% yeast extract). Fermentation was performed with mixing at 600 rpm at 60° C. with initial pH of 8.0 and aeration (0.6 L/min). The growth increased from O.D. 0.5 to 3.0 which was measured as turbidity at 660 nm by a spectrophotometer. The lipolytic enzyme activities were determined according to the assay methods described previously. The cells were separated from culture broth by centrifugation. Lipolytic enzymes were recovered by ultrafiltration of the supernatant followed by dialysis and finally the dialyzed preparation was freeze-dried.

EXAMPLE 2

Fermentation with Shake Flasks

The inoculum (1%) was transferred to 1 L shake flask containing 200 mL of fermentation medium (Basic medium contained 0.5% corn oil, 0.5% Tween, 80, and 0.1% yeast extract, pH 9.0) and incubated at 60° C, 200 rpm shaking for 15-18 hrs. The growth $O.D_{660}$ increased from 0.4 to 2.0. The lipolytic enzyme activities in final fermentation broth was 0.5 U/mL. The lipolytic enzymes were then separated and prepared as described in Example 1.

Taxonomic Identification of the Bacterial Isolate

The preferred strain has been characterized as Bacillus spp. according to the methods described in "The Genus Bacillus", by R. E. Gordon et al.[2]. U.S. Govt. Printing Office, 1973. This strain is able to grow in a wide pH range of 5.0-9.0 at high temperatures (45°-65° C.) and it produces extracellular lipolytic enzymes and utilizes oil substrates such as corn oil, olive oil or coconut oil.

Methods Used in Characterization of Lipolytic Activities

Measurement of Optimum pH Condition

A reaction mixture using buffers (100 mM) at pH's in the range of 2.5 to 11.0, (glycine-hydrochloride at pH 2.5 to 4.5, phosphate at pH 5 to 6.5, tris-hydrochloride at pH 7 to 9.5 and glycine-sodium hydroxide at pH 10 to 11) was employed. The activities were measured in the same manner as in the above description. The maximum activity was taken as 100% and relative activities were then calculated.

Measurement of Optimum Temperature Condition

A reaction mixture using Tris-hydrochloride buffer (100 mM), at pH 9.5 was employed. Activities were measured after 1 hour incubation with 180 r.p.m. shaking at desired temperatures by Rhodamine 6G method. The maximum activity was taken as 100% and relative activities were then calculated.

Measurement of pH Stability

An enzyme solution was added in glycine-hydrochloride buffer (100 mM) at pH 2.5 to 5, in phosphate buffer (100 mM) at pH 5 to 6.5, in Tris-hydrochloride buffer at pH 7 to 9, in arginine sodium hydroxide buffer at pH 10 to 12 and kept at 37° C. for 15 hours. Residual activities were measured in the same manner as in the above description.

Measurement of Temperature Stability

An enzyme solution (pH 9) was kept at 23° C., 60° C., 75° C., 90° C., for a period from 10 min to 24 hrs. The mixture was cooled in an ice bath for 10 min. Residual activities were measured in the same manner (pH 9.5, 60° C.) as described above.

Measurement of Hydrogen Peroxide Resistance

To an aliquot of enzyme solution containing a known amount of activity, different amounts of hydrogen peroxide were added to final concentration of 0.5, 1, 2, and 4% respectively. These were kept at 30° C. for different periods of time. Then hydrogen peroxide contained in enzyme solution was eliminated by dialysis against water. Residual activities were measured by the analytical methods described above.

Effects of the Presence of Various Proteases

To the reaction mixture, subtilisin or thermolysin was added to a final concentration of 0, 2, 4, 6, 8, and 10U/mL, respectively. The enzyme activities were measured at 60° C., pH 9.5 according to techniques described above.

RESULTS

Production of Thermostable Lipase

The lipase of the present invention is produced by submerged aerobic culture of biologically pure cultures of Bacillus sp. A30-1 ATCC No. 53841 which excretes the lipolytic enzymes into the medium. The strains to be used are, in particular, strain ATCC No. 53841 or other organisms derived therefrom by selection or artificial mutation or even by incorporating genetic information from said Bacillus sp. A30-1 into other hosts that code for the production of lipolytic enzymes by culturing in appropriate culture medium. The microorganism can readily grow on simple defined medium (Table 1). Enzyme production is stimulated by the addition of Tween 80 (1%) when corn oil is used as substrate. The cultivation can be carried out in the temperature range of 45°-65° C. and pH range of 6.0 to 9.0. However, growth temperature of 60°-65° C. and pH between 7.0 and 9.0 is preferred. The enzyme may be purified using 8% preparative PAGE. The purified lipase was identified by both isoelectric focusing and SDS-PAGE methods as a single band protein which was further confirmed by HPLC. The lipase had an isoelectric point of 5.15.

Initial Characterization of the New Lipase

The lipase produced by Bacillus sp. A30-1 (ATCC No. 53841) was characterized as follows:

1. Optimum pH condition

The activities of the lipase were measured according to the assay method described. The enzyme is functional over a wide range of pH, from 4.5 to 10.0. Although the optimum activity is at pH 9.5, this enzyme showed 90% of optimum activity at different pH, between 4.5 and 10.0.

2. Optimum temperature condition

The activities were tested at temperatures from 23° C. to 95° C. The lipase showed optimum activity at 60° C. and also displayed 90% and 45% of optimum activity at 70° C. and 80° C., respectively.

3. pH stability

To estimate the pH stability of lipase, an enzyme solution at various pHs was kept at 37° C. and activity checked after 15 hrs incubation. The enzyme retained 90-95% of the original activity after it was incubated at pHs from 5 to 11 for 15 hrs.

4. Temperature stability

The temperature stability of the enzyme was also investigated with results as shown in Table 2. It retains 100% of the original activity after being heated at 75° C.

for 30 min and 65% after being heated at 90° C. for 10 min. The half-life at 75° C. was found to be 8 hrs.

5. Fatty acid specificity against triacylglyceride with single acid

Various kinds of triacylglycerides with fatty acids having different carbon chain lengths were used for specificity study of the lipase.

Table 3 shows the relative lipolytic activity of this lipase to some triglycerides with single fatty acid in relation to the activity on triolein (taken as 100%). This lipase showed activity towards triglycerides containing saturated fatty acids having carbon chain lengths of C16:0, C18:0 as well as the ones of higher carbon chain length e.g., C20:0, C22:0 (Table 3).

6. Specificity to natural fats and oils

Relative enzyme activities of this lipase on some natural oils and fats in relation to the activity on olive oil taken as 100% has been presented in Table 4.

7. Hydrogen peroxide

The enzyme keeps 100% and 60% of the original activity after being incubated with 0.5% hydrogen peroxide for 1 hr and 19 hrs, respectively. After 5 hrs incubation with 4% hydrogen peroxide, the residual activity was 75%.

8. Effect of subtilisin

Two proteases, subtilisin (detergent protease) and thermolysin, both from Sigma Chemical Co. were used in the enzyme assay mixture to determine the effect of proteases on the lipase activity. Using 5 U/mL of subtilisin, 60% of the original activity remained. With 8 U/mL thermolysin, 90% of the activity remained.

9 Molecular weight

It has an approximate molecular weight of about 65,000 (i.e. 65K on SDS-PAGE).

It will be apparent to those skilled in the art that the lipase of the present invention has an optimum activity at 50° C. to 60° C. with a superior thermostability that has not been described for other lipases obtained from the mesophilic Bacillus spp. reported in the literature. Furthermore, the lipase of the present invention is not only active but is also stable in the wide pH range of 4 to 10. These unique properties of the lipase make this enzyme useful in fat hydrolysis as well as detergent formulations. The resistance of the lipase to hydrogen peroxide and alkaline proteases which are the components in detergents show that this lipase is environmentally compatible for its application in detergents.

The thermostability and pH stability of the lipase make it a potential candidate for tallow hydrolysis. For the production of desirable fatty acids and glycerol from tallow a pH range of 5-6 and temperature of 50° C. to 60° C. is desired.

The lipase of the present invention may also be suitable for synthesis of specialty chemicals such as surfactants, esters and such.

TABLE - 1:

Composition of the growth medium used to prepare stock and seed culture, and to grow the Bacillus sp. A30-1 ATCC No. 53841 for the production of Lipase.

| Ingredients | Concentration (G/L) |
|---|---|
| SEED MEDIUM | |

TABLE - 1:-continued

Composition of the growth medium used to prepare stock and seed culture, and to grow the Bacillus sp. A30-1 ATCC No. 53841 for the production of Lipase.

| Ingredients | Concentration (G/L) |
|---|---|
| $CaCl_2.2H_2O$ | 0.05 |
| Corn oil | 10.00 mL/L |
| $KH_2PO_4$ | 0.50 |
| $MgSO_4.7H_2O$ | 0.50 |
| $NH_4Cl$ | 1.00 |
| pH | 9.00 |
| NaCl | 1.00 |
| Trace Minerals Solution | 10.00 mL/L |
| Vitamin Solution | 10.00 mL/L |
| Yeast Extract | 0.10 |
| TRACE MINERALS SOLUTION | |
| $H_3BO_3$ | 0.50 |
| $CaCl_2.2H_2O$ | 20.00 |
| $CoCl_2.6H_2O$ | 200.00 |
| $CuSO_4.5H_2O$ | 0.40 |
| $FeSO_4.7H_2O$ | 130.00 |
| KI | 0.10 |
| $MnCl_2.4H_2O$ | 100.00 |
| $Na_2MoO_4$ | 10.00 |
| $Na_2SeO_3$ | 20.00 |
| $Na_2WO_4$ | 20.00 |
| $NiSO_4.6H_2O$ | 30.00 |
| $ZnCl_2.2H_2O$ | 100.00 |
| VITAMIN SOLUTION | |
| Biotin | 2.00 |
| Crystalline cyanocobalamin ($B_{12}$) | 0.10 |
| Folic Acid | 2.00 |
| Lipoic (thioctic) acid | 5.00 |
| Nicotinic acid (niacin) | 5.00 |
| Pantothenic acid | 5.00 |
| p-aminobenzoic acid (PABA) | 5.00 |
| Pyridoxine HCl ($B_6$) | 10.00 |
| Riboflavin ($B_2$) | 5.00 |
| Thiamine HCl ($B_1$) | 5.00 |

TABLE 2.

Heat stability of Bacillus sp. A30-1 ATCC No. 53841.

| Temperature | Incubation time (hr) | Activity (%) |
|---|---|---|
| 23° C. | 18 | 90 |
| | 24 | 87 |
| 60° C. | 18 | 82 |
| | 24 | 75 |
| 75° C. | 0.5 | 100 |
| | 1 | 97 |
| | 2 | 90 |
| | 3 | 73 |
| | 4 | 60 |
| | 8 | 50 |
| 90° C. | 10 min | 65 |
| | 15 min | 63 |
| | 30 min | 40 |
| | 60 min | 40 |

TABLE 3.

Relative rate of hydrolysis of various triglycerides by Bacillus sp. A30-1 ATCC No. 53841.

| Triglycerides | "C" No. | Average Activity (%) |
|---|---|---|
| Tricaprylin | C8:0 | 97 |
| Tricaprin | C10:0 | 116 |
| Trilaurin | C12:0 | 160 |
| Trimyristin | C14:0 | 97 |
| Tripalmitin | C16:0 | 55 |
| Tristearin | C18:0 | 48 |
| Triolein | C18:1 | 100 |
| Trilinolin | C18:2 | 99 |
| Triarachidin | C20:0 | 37 |
| Tribehenin | C22:0 | 6.7 |

TABLE 4.

Relative rate of hydrolysis of fats and oils by Bacillus sp. A30-1 ATCC No. 53841.

| Oil | Activity (%) |
|---|---|
| Corn | 102 |
| Olive | 100 |
| Cottonseed | 110 |
| Coconut | 103 |
| Peanut | 94 |
| Soybean | 109 |
| Linseed | 83 |
| Wheat Germ | 107 |
| Butter | 45 |
| Beef Tallow | 75 |
| Pork Lard | 93 |

REFERENCES

1. Tserng, K., Kliegman R. Miettinen, E., Kalhan, S., (1981). J. Lipid Res., 22:852–858.
2. Gordon, R. E., W. C. Haynes, C. H-N. Pang. 1973. The Genus Bacillus. Agricultural Research Service, USDA. U.S. Govt. Printing Office, Washington, D.C.

It will be appreciated that lipolytic productivity may be enhanced through mutation of the producing organism or by genetic recombination techniques. Therefore, the scope of the invention should not be limited to the specific strain of the organism described because any organism capable of producing the same enzyme is intended to be included in the scope of the present invention.

We claim:

1. An essentially purified, thermostable and alkalophilic lipase from Bacillus Sp. A30-1 ATCC 53841, said lipase having an optimum pH of 9.5, an isoelectric point of 5.15, a molecular weight of about 65,000 and retaining approximately 100% of its original activity upon being heated at 75° C. for 30 minutes.

* * * * *